United States Patent
Choudary et al.

(10) Patent No.: US 6,797,038 B2
(45) Date of Patent: Sep. 28, 2004

(54) ADSORBENTS, METHOD FOR THE MANUFACTURE THEREOF AND PROCESS FOR THE SEPARATION OF UNSATURATED HYDROCARBONS FROM GAS MIXTURE

(75) Inventors: Nettem Venkateswarlu Choudary, Gujarat (IN); Prakash Kumar, Gujarat (IN); Vijayalakshmi Ravi Puranik, Gujarat (IN); Sodankur Garadi Thirumaleshwara Bhat, Gujarat (IN)

(73) Assignee: Indian Petrochemicals Corporation Limited, Gujarat (IN)

( * ) Notice: Subject to any disclaimer, the term of this patent is extended or adjusted under 35 U.S.C. 154(b) by 0 days.

(21) Appl. No.: 10/274,825

(22) Filed: Oct. 21, 2002

(65) Prior Publication Data

US 2003/0097933 A1 May 29, 2003

(30) Foreign Application Priority Data

Nov. 23, 2001 (IN) ................................. 1120/MUM/2001

(51) Int. Cl.$^7$ ............................................... B01D 53/04
(52) U.S. Cl. ............................... 95/144; 95/95; 95/900; 96/108; 502/407; 502/415
(58) Field of Search ........................... 95/95, 143, 144, 95/900; 96/108; 502/405, 407, 415

(56) References Cited

U.S. PATENT DOCUMENTS

| | | | | |
|---|---|---|---|---|
| 2,685,607 A | * | 8/1954 | Pevere et al. .................. | 95/144 |
| 2,696,497 A | * | 12/1954 | Cines et al. ................ | 562/125 |
| 4,382,879 A | * | 5/1983 | Funabashi et al. .......... | 502/407 |
| 4,546,094 A | * | 10/1985 | Hirai et al. .................. | 502/402 |
| 4,747,855 A | * | 5/1988 | Hirai et al. .................... | 95/106 |
| 4,917,711 A | * | 4/1990 | Xie et al. ...................... | 95/106 |
| 4,933,159 A | * | 6/1990 | Nowack et al. ........... | 423/245.1 |
| 5,024,683 A | * | 6/1991 | Tooley et al. .................. | 95/141 |
| 5,175,137 A | * | 12/1992 | Golden et al. .............. | 502/417 |
| 5,593,933 A | * | 1/1997 | Chattha et al. ............. | 502/317 |
| 6,033,461 A | * | 3/2000 | Yang et al. .................... | 95/129 |
| 6,293,999 B1 | * | 9/2001 | Cheng et al. ................... | 95/96 |
| 6,296,688 B1 | * | 10/2001 | Cheng et al. .................. | 95/101 |
| 6,406,521 B1 | * | 6/2002 | Cheng et al. ................... | 95/98 |
| 6,488,741 B2 | * | 12/2002 | Olson ........................... | 95/144 |
| 6,517,611 B1 | * | 2/2003 | Kuznicki et al. ............. | 95/144 |
| 2002/0005118 A1 | * | 1/2002 | Cho et al. ..................... | 95/143 |

* cited by examiner

Primary Examiner—Robert H. Spitzer
(74) Attorney, Agent, or Firm—Ladas & Parry

(57) ABSTRACT

An adsorbent for selective adsorption of unsaturated hydrocarbons from its mixture with saturated hydrocarbons, carbon dioxide, carbon monoxide, permanent gases or mixture thereof. The adsorbent includes a silver or copper compound in an amount of 1 to 70 wt % and a substrate in 30 to 99% wt %. Also a method for the manufacture of an adsorbent, which includes impregnating or dispersing a silver (I) or copper (I) compound on a mesoporous substrate or support to form a composite material and subjecting the composite material to heat treatment. Also, a process for separating ethylene and/or propylene from gas mixtures containing them by passing a stream of the gas mixture through a mass of the adsorbent at a temperature from 0° C. to 170° C. and a pressure from 0.1 to 100 atmospheres and releasing the adsorbed ethylene and/or propylene by lowering pressure and/or increasing temperature.

43 Claims, 4 Drawing Sheets

Fig: Nitrogen adsorption-desorption isotherms and pore size distribution on HMS (Dodecylamine) at 77K.

Fig: Nitrogen adsorption-desorption data and pore size distribution on HMS (Hexadecylamine) at 77K.

Fig: Nitrogen adsorption-desorption isotherms and pore size distribution on HMS (Brij-97) at 77K.

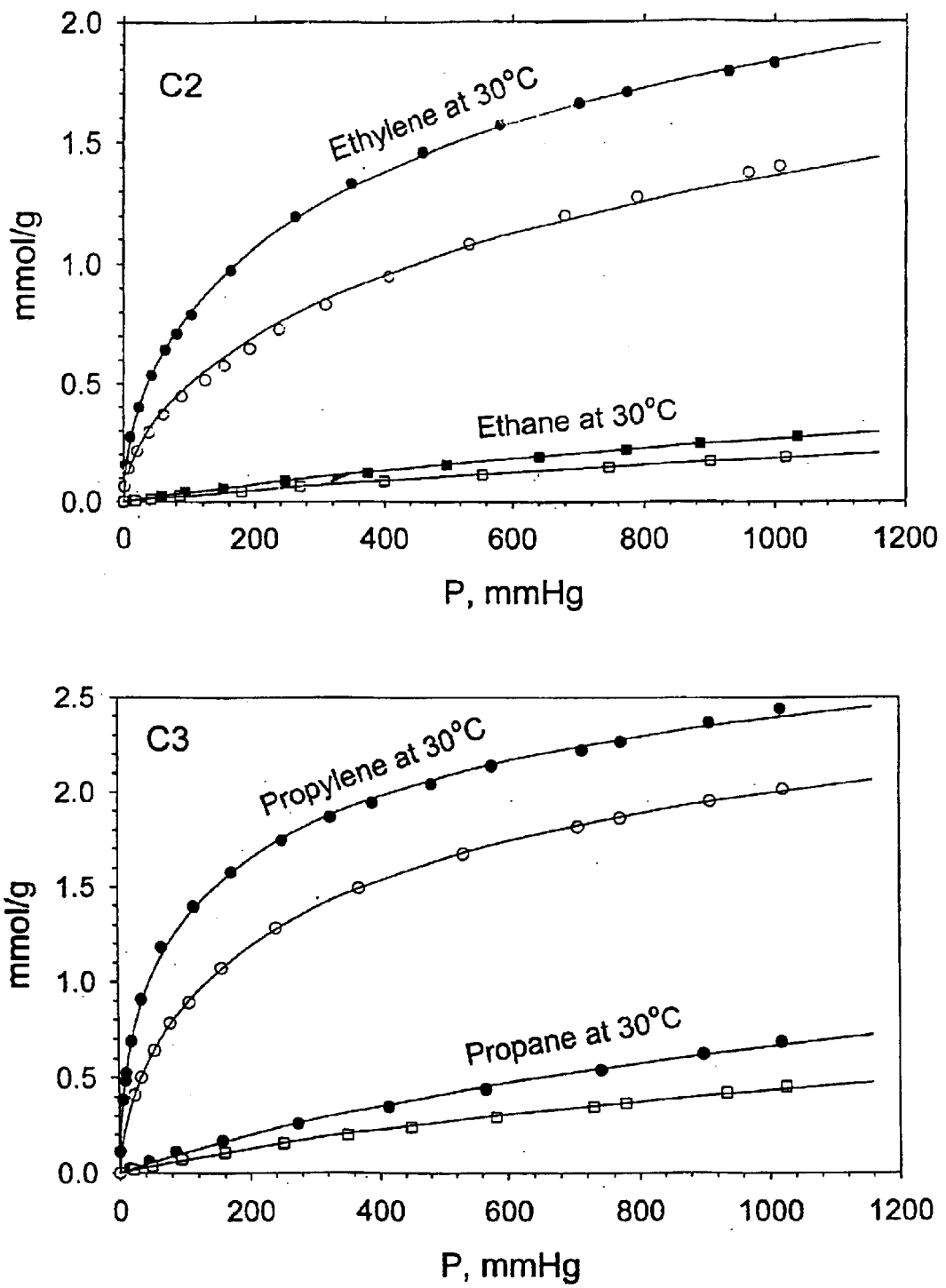
Fig. 3. Adsorption isotherms of C2, C3 gases on adsorbent Sample-1 (Example-2)
(closed sympols at 30°C and open symbols at 50°C)

ADSORBENTS, METHOD FOR THE MANUFACTURE THEREOF AND PROCESS FOR THE SEPARATION OF UNSATURATED HYDROCARBONS FROM GAS MIXTURE

TECHNICAL FIELD OF THE INVENTION

This invention relates to novel adsorbents useful in selective adsorption of unsaturated hydrocarbons manufacture of such adsorbents and process for the separation of unsaturated hydrocarbons using such adsorbents. More specifically, this invention relates to an adsorbent having a high degree of selectivity and affinity for olefin molecules and also having high adsorption capacity for olefins, and a process for producing the same. More specifically, this invention relates to ethylene and/or propylene separation process employing a specially prepared adsorbent to effectively separate ethylene and/or propylene from a gas mixture containing ethylene and/or propylene together with one or more components selected from the group consisting $H_2$, N, Ar, He, $CH_4$, $C_2H_6$, $C_3H_8$, $CO_2$, and CO in an efficient manner using the adsorbent of the present invention. The adsorbents of the present invention display high adsorptive capacity for unsaturated hydrocarbons such as ethylene and propylene.

PRIOR ART

Unsaturated hydrocarbons such as ethylene, propylene and butene are basic raw materials in synthetic chemistry. These are produced by naphtha/natural gas cracking or by dehydrogenation of paraffins. Invariably, these are obtained as mixtures necessitating separation before their use. Traditionally separations of ethylene from ethane and propylene from propane have been achieved by low temperature and/or high pressure distillation. These separations are highly energy intensive and difficult to achieve. Separation of mixture of ethane-ethylene is carried out at −25° C. and 320 psig in a distillation column containing over 160 trays and propane-propylene at −30° C. and 30 psig pressure in a distillation column containing over 200 trays. Separations of ethane-ethylene and propane-propylene by distillation are the largest energy consuming separation processes in petrochemical industry. Furthermore, demand for ethylene and propylene is ever increasing. World wide ethylene capacity of about 100 million metric tons (mmt) per year is projected to grow to 122.1 mmt/y by 2005. For the past several years, various researchers have been working on the development of alternative technologies such as adsorption, chemical absorption and membrane separation processes. Of the various alternative technologies adsorption process appears to be the most promising. Adsorbent forms heart of any adsorption process. An adsorbent suitable for the separation of light olefin/paraffin gas mixture should have high adsorption capacity and selectivity for either olefin or paraffin. Adsorbed component should be able to desorb easily by simple chemical engineering operation such as by increasing the temperature or by reducing the pressure. Conventional adsorbents such as activated alumina, activated carbon, silica gel and zeolites known in the prior art do not show good selectivity for olefins or paraffins. Hence, development of a suitable adsorbent has become a key factor in the development of adsorption process.

The adsorbents such as ion exchanged zeolites, polymer supported silver chloride, copper-containing resins etc. known in the prior art exhibiting selectivity for ethylene or propylene suffer from one or more drawbacks such as slow adsorption kinetics, poor adsorption capacity and/or selectivity. Recently, Yang an Kikkinides (Ref, AIChE J. 41,509, 1995) and Cho and co-workers (Ind. Eng. Chem. Res., 36, 27749, 1997) have reported more promising adsorbents. Among the adsorbents reported by them, Ag+ resin and $CuCl/Al_2O_3$ showed high olefin adsorption capacity and good selectivity. However, ethylene and propylene sorption kinetic on $Ag^+$ resin are slow. $CuCl/Al_2O_3$ is a CuCl dispersed on y-$Al_2O_3$ by monolayer dispersion technique and hence, is obtained in a powder form. For commercial use, this adsorbent needs to be shaped into pellets, which leads to reduction in adsorption capacity and selectivity. Furthermore, adsorbent formulations prepared sing Cu(I) compounds are unstable and easily get oxidized to Cu(II) leading to loss in adsorption capacity and selectivity of the adsorbent. Xie et al, (Advances in Catalysis, 1, 37, 1990) have also reported a series of adsorbents containing Cu(I). These were also prepared in powder form. Hence, these adsorbents also suffer from the above mentioned drawbacks. More recently Cho et al invented olefin selective adsorbents exhibiting superior adsorption capacity, selectivity and rates of adsorption. These were prepared by dispersing silver compound on conventional supports such as activated alumina and acid activated clay. These adsorbents possess high adsorption capacity and selectivity for olefins over paraffins compared to those reported in the prior art. However, due to ever changing business requirements and demands, it is desirable to have adsorbents exhibiting even higher adsorption capacity, selectivity and/or reversibility for efficient separation of hydrocarbon gases. The present invention now seeks to meet such demands by providing novel adsorbent formulations and methods exhibiting very high adsorption capacity, selectivity and reversibility for olefins over saturated hydrocarbons.

OBJECTS OF THE PRESENT INVENTION

It is an object of the present invention to provide an adsorbent composition exhibiting high adsorption selectively and capacity for unsaturated hydrocarbons.

Yet another object of this invention is to provide a method for the production of an adsorbent possessing high adsorption capacity for selectively adsorbing unsaturated hydrocarbons.

It is yet another object of this invention is to provide improved, stable solid adsorbents) in powder, pellet or bead form for selective adsorption of saturated hydrocarbons, which adsorbent is a composite comprising (a) a silver compound or copper and (b) a suitable mesoporous substrate having a sufficiently high surface area, and highly suitable pore size distribution and which is obtainable by a process comprising dispersion/impregnation of silver compound in the support and heat treatment of the resulting composite material.

Yet another object of this invention to provide a process for the separation of ethylene, propylene and butylenes either individually or as mixture from a hydrocarbon stream containing ethylene, propylene or butylenes or mixture of together with one or more components selected from such gases as $H_2$, $N_2$, Ar, He, $CH_4$, $C_2H_6$, $C_3H_8$, $CO_2$ and CO using a mass of adsorbent.

Yet another object of this invention is to effect the above separation process at conditions of moderate temperatures (0–1 SOT) and pressures (0.1 to 100atmospheres).

SUMMARY OF THE INVENTION

It has now been found that a group of solid adsorbents in the form of powder, granules or pellets have improved adsorptive capacity, selectivity and reversibility for ethylene and/or propylene not known in the prior art and that they can be produced by a process as described below. These adsorbents comprise (a) a silver or copper compound and (b) a mesoporous substrate. These adsorbents are highly stable and are capable of reversibly adsorbing substantial quantity of ethylene and/or propylene at room temperature. The rates of adsorption of ethylene and/or propylene are also very fast in these adsorbents.

Accordingly, the present invention provides an adsorbent for selective adsorption of unsaturated hydrocarbons from its mixture with saturated hydrocarbons, carbon dioxide, carbon monoxide, permanent gases or mixture thereof comprising of:

Silver or copper compound 1 to 70 wt %

Substrate 30 to 99%

The present invention also provides a method for the manufacture of an adsorbent for use in selective adsorption of unsaturated hydrocarbons or mixtures thereof from a mixed gas, which comprises impregnating or dispersing a silver (I) or copper (I) compound on a mesoporous substrate or support to form a composite material and subjecting said composite material to heat treatment.

In another important aspect, the present invention also relates to a process for separating ethylene and/or propylene from gas mixtures containing them by passing a stream of said gas mixture through a mass of said adsorbent at a temperature from 0° C. to 170° C. and a pressure from 0.1 to 100 atmospheres and releasing the adsorbed ethylene and/or propylene by lowering pressure and/or increasing temperature.

BRIEF DESCRIPTION OF THE DRAWINGS

FIG. 2 are graphs showing adsorption isotherms of C2, C3 gases on the adsorbent of the invention described in Example 2, below.

DETAILED DESCRIPTION OF THE INVENTION

Figure 1A:
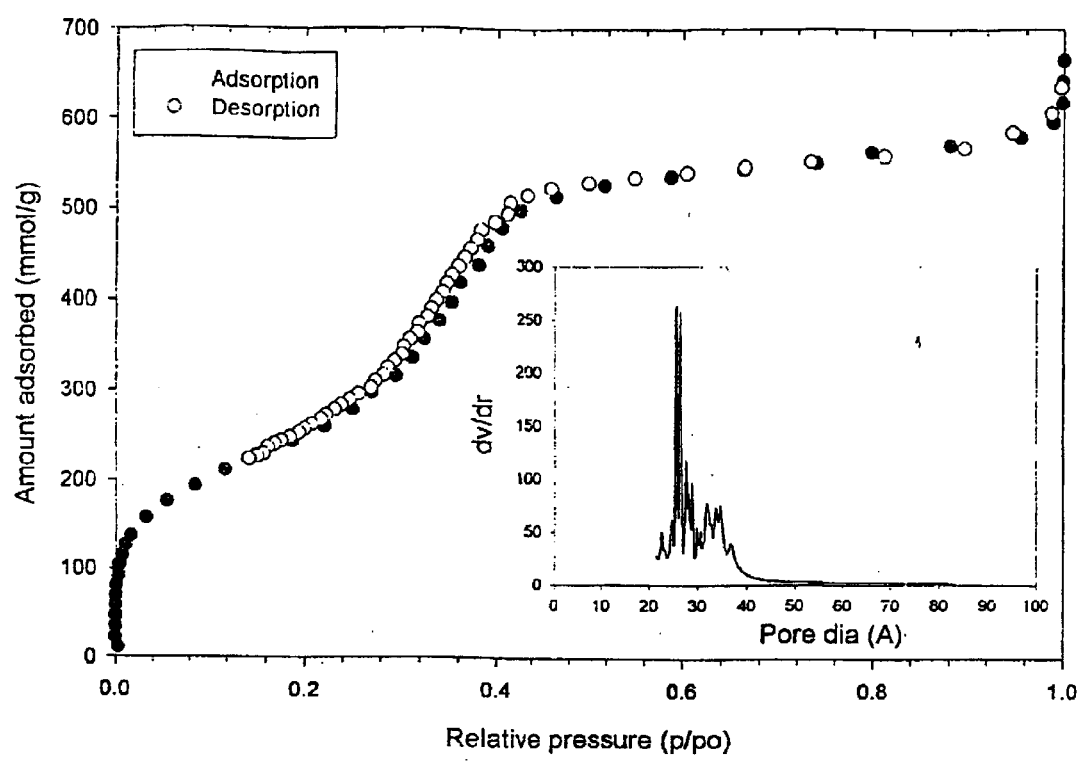
FIG. 1A is a graph showing nitrogen adsorption-desorption isotherms and pore size distribution on HMS (Dodecylamine) at 77K of an adsorbent of the invention.

The adsorbents of this invention are obtained by dispersion of silver or copper compound on the surface of a mesoporous silica or alumina substrate as active compound. The dispersion of silver or copper compound is achieved either by impregnation or by solid state monolayer dispersion. Many silver(I), copper(I), silver(II) or copper (II) compound or their mixtures can be used as active compound. When silver (II) or copper (II) compound is used as active metal compound, silver(II) or copper(II) needs to be reduced to silver (I) or copper(I) respectively in a reducing atmosphere. Some of the representative examples of the silver compounds which can be suitably utilized in the practice of this invention are silver nitrate, silver halides such as silver chloride, silver bromide and silver iodide, silver perchlorate, silver tetrafluoroborate, silver carboxylates such as silver formate and silver acetate, and silver oxide. Preferred silver compounds are silver nitrate, silver acetate, silver sulfate, silver chloride and silver tetrafluoroborate. Some of the representative examples of the copper compounds, which can be suitably utilized in the present invention, include copper chloride, copper sulfate, and copper acetate.

Solid supports (substrate) required for the preparation of the selective adsorbents plays an important role. The synthesis of first mesoporous molecular sieve MCM-41 (Mobil 1992 reference) was reported in 1992 with pore sizes in the range of 1.5 to over 10 nm using cationic surfactant templates. Tanev and Pinnavaia in 1995 proposed a neutral (S°I°) templating route for the synthesis of mesoporous molecular sieves based on hydrogen bonding and self-assembly between neutral primary amine surfactants (S°) and neutral inorganic precursors (1°). Neutral templating route results in mesoporous materials with better hydrothermal stability. Further, template can be completely extracted from the pores of the mesoporous materials for reuse. This eliminates the need for calcination of the surfactant. In the present invention three types of mesoporous substrates are used. These are hexagonal mesoporous silica (HMS), SB A-15 and mesoporous alumina.

In the present invention the mesoporous substrates are used either in powder form or formed bodies. Substrate bodies are formed by extrusion or granulation as described below.

The substrate is obtained in pellets form by (a) mixing with a suitable inorganic binder thoroughly in a ball mill to obtain a homogeneous mixture of substrate-binder, (b) forming dough by the addition of required quantity of water and optionally suitable extrusion aid such as polyvinyl alcohol, methyl cellulose, acetic acid, ligno sulfonate or sotta silicate in a kneeding machine, and (c) extrusion through an extruder having a suitable die. To obtain pellets in spherical shape, the substrate-binder mixture obtained above after step (a) is converted to spherical pellets in a pan granulator by simultaneous addition of powder mixture and spraying water. The amount of inorganic binder employed can vary from 5 to 50% preferrably from 10 to 30% by weight of the adsorbent binders that can be employed include hydrated alumina, kaolinite, sodium silicate solution.

Silver or copper compound solution is first prepared by dissolving calculated amount of active metal compound in a suitable solvent. The total volume of active metal solution required is obtained by measuring the total pore volume of the substrate. The active metal compound prepared above is then mixed with a known quantity of activated substrate and equilibrated for a period or 0.1 to 24 hrs preferably for 1 to 4 hrs. The excess solvent is then removed from the resultant mixture by heating and/or purging with air/inert gas or by applying vacuum. The adsorbent is then dried in an oven at 90–110° C. with or without inert flow. The dried adsorbent is then calcined at a temperature in the range of 100 to 600° C. for a period of time from about 0.1 to about 100 hrs, preferably from about 1 to 10 hours. The heating step can be conducted in a suitable atmosphere such as nitrogen and helium.

Representative examples of the solvent that can be suitably used include, for example, water, hydrochloric acid containing aqueous solution, nitric acid containing aqueous solution, ammonium hydroxide solution, primary or secondary alcohols having 1 to 7 carbon atoms, acetone, ethyl acetate, hydrocarbons having 4 to 7 carbon atoms, propionitrile, and acetonitrile.

The adsorbent of the present invention can also be prepared by physically mixing silver or copper compound in solid form to substrate in powder form. The amount of silver in the form of the compound is preferably from 1 to 70% by weight of adsorbent composition. The resultant solid mixture is heated at a temperature in the range of 30 to 600° C. preferably at 100 to 250° C. for a period of time from about 0.1 to about 100 hrs, preferably from about 1 to 10 hours. The heating step can be conducted in a suitable atmosphere such as nitrogen and helium.

The adsorbent of the present invention can also be prepared in a pellet form as described herein: (a) Silver or copper compound and inorganic binder such as, hydrated alumina, bentonite, attapulgite, sepiolite, kaolinite are thoroughly mixed with a suitable substrate, (b) the mixture thus obtained is converted to dough by adding a suitable solvent and mixing in a kneading machine, (c) The dough thus obtained is extruded through an extruder having a die plate (d) The extruded pellets are dried at room temperature followed by drying at 90–120° C. in an oven, (e) The dry adsorbent is then calcined at a temperature in the range of 100 to 600° C. for a period of time from about 0.1 to about 100 hrs, preferably from about 1 to 10 hours. The heating step can be conducted in a suitable atmosphere such as nitrogen and helium.

The adsorbents of this invention described above can be used to separate ethylene or propylene from mixed gases. The separation process comprises passing a stream of the mixed gas through an adsorber bed charged with the adsorbent(s) of the invention. Ethylene and/or propylene, which are selectively adsorbed, can be readily desorbed either by lowering the pressure or by increasing the temperature of the adsorber bed resulting in a regenerated adsorbent. The adsorbent so regenerated can be reused as an adsorbent for the separation of ethylene and/or propylene from the mixed gas. This separation process can also purify raw material gases wherein ethylene and/or propylene are present as impurities.

The invention will now be further illustrated by the following Examples. The adsorption capacity and selectivity data given in these Examples are obtained by measuring adsorption isotherms by volumetric set-up. Adsorption rates and adsorption reversibility given in the examples is are obtained by measuring adsorption and desorption uptakes in CAHN 1100 microbalance system. In a typical a adsorption-desorption isotherm measurement, a known quantity of the adsorbent was loaded in volumetric set-up or the CAIN 1100 microbalance system and activated under vacuum (to $10^{-4}$ mmHg) at a suitable temperature for several hours. The adsorbent was then cooled to room temperature under vacuum. Adsorption isotherm was measured by admitting pulses of pure hydrocarbon gas into the adsorption set-up. After each adsorption isotherm measurement, desorption experiment was also carried out to check the reversibility of the adsorption isotherm. In any adsorption process both adsorption capacity and the working capacity of an adsorbent are very important. The working capacity of an adsorbent is the difference between the adsorption capacity at a predetermined partial pressure of an adsorbate and the amount retained at lower partial vapor pressure. The adsorption uptake was measured by admitting pure hydrocarbon gas into the CAHN balance at 1 atmosphere and recording the weight gain as a function of time.

All of the given Examples are merely for the purpose of illustration and are not to be regarded as limiting the scope of the invention or the manner in which it can be practiced.

EXAMPLE-1

A homogeneous solution was obtained by dissolving 5.2 Ig of dodeclamine in 42.08 g of ethyl alcohol in 600 ml beaker. To this solution 53.07 g of double distilled water was added with vigorous stirring. To the resultant solution, 20.89 g of tetraethyl orthosilicate (TEOS) was added drop wise with continuous stirring at room temperature. Stirring was continued for another forty five minutes followed by aging for 24 hours at room temperature. The resultant solid product, hexagonal mesoporous silica, HMS-1 was recovered by filtration, washing with water and water-alcohol mixture. HMS-1 was then air dried followed by oven drying for 8 hours. Dodecylamine was almost completely recovered from HMS-1 pores by refluxing with ethyl alcohol. The resultant mesoporous silica was then dried and calcined at 600° C. for 4 hours. The yield of HMS product was 97% by weight. It was characterized by XRD which exhibited characteristic peak at 2.3 (2θ). Surface area (1076 m²/g), average pore size (2.5 nm) and pore volume (0.99 cc/g) were obtained from measured nitrogen adsorption and desorption isotherms at −196° C. and shown in FIG. 1.

EXAMPLE-2

Part of the substrate HMS-1 obtained from Example-1 was compressed into a pellet in a die by applying 5 tons of pressure. The resultant pellet was broken into small particles of about 1 mm and activated in a furnace at 250° C. for 4 hours. Silver salt solution was impregnated on the activated substrate as described herein. About 0.4 g of silver nitrate ($AgNO_3$) was dissolved in double distilled water. The aqueous silver salt solution thus obtained was added to predetermined quantity of activated substrate and thoroughly mixed. The resultant mixture was allowed to equilibrate for 3 hours. The excess moisture was removed by purging with nitrogen at room temperature. The resultant adsorbent, Sample-1 thus obtained was dried at 110° C. in an oven for 10 hours followed by activation in a muffle furnace at 200° C. for 4 hours. The adsorbent has the chemical composition of 30.0 wt % $AgNO_3$ and 70.0 wt % $SiO_2$. Adsorption isotherms of ethylene, ethane, propane, methane, acetylene, carbon monoxide, carbon dioxide, and nitrogen were measured at 30° C. and 50° C. The adsorption isotherms C2 and C3 gases are shown in FIG. 2. The adsorption data at 30° C. and 1 atm are given in Table 1. The adsorbent absorbed 1.70 and 2.27 mmol/g of ethylene and ethane respectively at 30° C. and 1 atm. Adsorption uptakes of ethylene and propylene measured on the above adsorbent at 30° C. show that about 90% of adsorption is complete within 5 minutes. On desorption at 30° C. by evacuation only (1 mmHg) 0.19 mmol/g of ethylene was retained on the adsorbent. However, on heating at 100° C. ethylene is completely desorbed. The adsorbent exhibited same adsorption capacity for ethylene on re-adsorption at 30° C. showing good reversibility of the adsorbent.

EXAMPLE-3

About 0.6 g of silver nitrate was impregnated on activated substrate obtained from Example-1 using the impregnation procedure employed in Example-2. The resultant adsorbent, Sample-2 was dried at 110° C. in an oven for 12 hours followed by activation in a muffle furnace at 210° C. for 5 hours. The chemical composition of the adsorbent is 38.0 wt % $AgNO_3$ and 62.0 wt % $SiO_2$. Adsorption of ethylene, ethane, propylene and propane were measured at 30° C. on this adsorbent and given in Table 1. The adsorbent adsorbed 1.92 mmol/g of ethylene and 2.49 mmol/g of propylene at 30° C. and 1 atmosphere. Adsorption selectivity for propylene and ethylene over corresponding paraffins was also high. Adsorption uptake of ethylene and propylene was also rapid. Over 90% of adsorption capacity was completed within 5 minutes. On desorption at 30° C. by evacuation only (1 mmHg) 0.14 mmol/g of ethylene was retained on the adsorbent. However, on heating at 100° C. ethylene is completely desorbed.

EXAMPLE-4

About 0.8 g of silver, nitrate was impregnated on activated substrate obtained as per the procedure given in Example-1 and using the impregnation procedure employed in Example-2. The resultant adsorbent, Sample-3, was then ed at 110° C. in an oven for 12 hours followed by activation in a muffle furnace at 210° C. for 5 hours. The chemical composition of the adsorbent was 44.4 wt % $AgNO_3$, the rest being $SiO_2$. Adsorption of ethylene and ethane were measured at 30° C. on this adsorbent. The adsorbent adsorbed 1.85 nmol/g of ethylene an 0.23 mmol/g of ethane at 30° C. About 90% of adsorption capacity was completed within 51 minutes. On desorption at 30° C. by evacuation only (1 mmHg) 0.16 mmol/g of ethylene was retained on the adsorbent. However, on heating at a higher temperature ethylene was completely desorbed indicating very good reversibility of the adsorbent.

EXAMPLE-5

Silver nitrate was impregnated on 1 g of activated substrate HMS-1 obtained from Example-1 using the impregnation procedure employed in Example-2. The resultant adsorbent, Sample-4 was dried at 110° C. in an oven for 12 hours followed by activation in a muffle furnace at 210° C. for 5 hours. The chemical composition of the adsorbent is 16.0 wt % $AgNO_3$ and 84.0 wt % $SiO_2$. Adsorption of ethylene, ethane, propylene and propane were measured at 30° C. on this adsorbent and given in Table 1. The adsorbent adsorbed 1.10 mmol/g of ethylene and 0.25 mmol/g of ethane at 30° C. and 1 atmosphere. Adsorption uptake of ethylene was also rapid. About 95% of adsorption capacity was completed with in 5 minutes. On desorption at 30° C. by evacuation only (1 mmHg) 0.12 mmol/g of ethylene was retained on the adsorbent.

EXAMPLE-6

4.4 g of activated silica substrate obtained as per the procedure described in Example-1 was thoroughly mixed with 0.6 g of bentonite clay using ball mill. The mixture was then converted to dough (paste) with the addition of required quantity of distilled water and extruded through a 1.5 mm diameter die. The sized extrudates, (about 2 mm long) were dried at room temperature followed by oven drying at 110° C. for 12 hours. The dry cylindrical pellets thus obtained were calcined at 550° C. for 6 hours in muffle furnace. About 2.0 g of silver nitrate was impregnated on the above calcined cylindrical pellets as per the impregnation procedure employed in Example-2. The resultant adsorbent, Sample-5, was dried at 110° C. in an oven for 10 hours followed by activation in a muffle furnace at 220° C. for 4 hours. The chemical composition of the adsorbent was 29.5 wt % $AgNO_3$, 68.0 wt % $SiO_2$>>1.6 wt % $Al_2O_{31}$, 0.3 wt % $Fe_2O$; 0.2 wt % MgO, the rest being oxides of alkali and alkaline earth metals. Adsorption of ethylene and ethane measured at 30° C. are given in Table 1. The adsorbent adsorbed 1.55 mmol/g of ethylene and 0.23 mmol/g of ethane at 30° C. About 92% of adsorption capacity was completed within 5 minutes.

EXAMPLE-7

About 3.5 g of activated mesoporous silica substrate obtained according to the procedure described in Example-1 was thoroughly mixed with 1.5 g aluminium trihydrate (Catapol from Vista Chemicals) in a ball mill. The mixture was then converted to dough (paste) by the addition of required quantity of aqueous acetic acid solution and extruded through a 1.5 mm diameter die. The sized extrudates (about 2 mm long) were dried at room temperature followed by oven drying a 110° C. for 12 hours. The dry cylindrical pellets thus obtained were calcined at 500° C. for 8 hours in muffle furnace. Silver nitrate solution was impregnated on the above calcined cylindrical pellets as per the impregnation procedure described in Example-2. The resultant adsorbent, Sample-6, was dried at 1 for 10 hours followed by activation in a muffle furnace at 200° C. for 6 hours. The chemical composition of the adsorbent thus obtained was 29 wt % $AgNO_3$, 57% $SiO_2$, and 14 wt % $Al_2O_3$. The adsorbent possessed high adsorption capacity (1.62 mmol/g at 30° C. and 1 atmosphere) for ethylene (Table 1). Only 0.29 mmol/g of ethane was adsorbed at 30° C. and 1 atmosphere. The rate of adsorption of ethylene was also fast and over 95% of adsorption capacity was achieved within first 5 minutes. On desorption at 30° C. by evacuation (1 mmHg) only 0.28 mmol/g of ethylene was retained on the adsorbent.

EXAMPLE-8

About 0.4 g of silver nitrate was thoroughly mixed with activated HMS-DA obtained from Example-1 using a mortar and pastel. The homogeneous mixture thus obtained was heated at 200° C. for 24 hours in a muffle furnace. The chemical composition of the resultant adsorbent, Sample-7 was 30.0 wt % of $AgNO_3$ and 70.0 wt % $SiO_2$. Adsorption of ethylene, ethane, propylene and propane measured at 30° C. and given in Table 1–2 showed high adsorption capacity. The adsorbent exhibited 1.59 mmol/g of ethylene and 1.83 mmol/g of propylene at 30° C. and 1 atmosphere. Adsorption capacity of the adsorbent for ethane and propane was low at 0.24 and 0.46 mmol/g. Adsorption uptakes of ethylene and propylene were also rapid. For example about 91% of ethylene adsorption capacity was completed within 5 minutes.

EXAMPLE-9

About 0.5 g of copper(I) chloride was thoroughly mixed with activated silica substrate obtained from Example-1 using a mortar and pestle. The mixture thus obtained was heated at 350° C. for 12 hours in a furnace under nitrogen purge. The chemical composition of the resultant adsorbent, Sample-8 was 34.0 wt % of CuCl and 64.0 wt % $SiO_2$. Adsorption of ethylene and ethane measured at 30° C. showed adsorption selectivity for olefin. The adsorbent exhibited 0.81 mmol/g of ethylene and 0.40 mmol/g of ethane at 30° C. and 1 atmosphere.

EXAMPLE-10

Silver acetate solution prepared by dissolving 0.4 g of silver acetate in dilute nitric acid was impregnated on an activated mesoporous silica substrate obtained by the procedure described in Example 1. The resultant adsorbent was dried at 110° C. for 4 hrs followed by calcination at 200° C. for 8 hrs under nitrogen flow. The chemical composition of the adsorbent, Sample-9, thus obtained is 29.5% $CH_3COOAg$ and 69.5% SiO2. The adsorbent adsorbed 2.02 mmol/g of ethylene and 0.28 mmol/g of ethane at 30° C. and 1 atmosphere pressure. The rate of adsorption was rapid. Over 90% of adsorption capacity was achieved within first 5 minutes. The adsorbed ethylene was completely desorbed

EXAMPLE-11

Silver chloride solution prepared by dissolving 0.4 g of silver chloride in ammonium hydroxide was impregnated on activated substrate obtained as described in Example 1. The mixture was allowed to equilibrate for 3 hours at room temperature. The excess solvent was dried at room temperature by purging with nitrogen gas. The resultant adsorbent was further dried at 110° C. for 4 hrs followed by calcination at 300° C. for 12 hrs under nitrogen flow. The chemical composition of adsorbent, Sample-10 thus obtained was 30% AgCl and 70% $SiO_2$. The adsorption data of ethylene and ethane measured at 30° C. are given in Table 1. The adsorbent adsorbed 1.10 mmol/g of ethylene and 0.38 mmol/g of ethane at 30° C. and 1 atmosphere pressure. The adsorbed ethylene was completely desorbed by evacuation at 100° C.

EXAMPLE-12

Silver sulfate ($Ag_2SO_4$) solution prepared by dissolving about 0 4 g of silver sulfate salt in ammonia solution was impregnated on activated substrate obtained as per the procedure described in Example 1. The mixture was allowed to equilibrate for 3 hrs at room temperature. The excess solvent was dried at room temperature by purging with nitrogen gas. The resultant adsorbent was further dried at 110° C. for 4 hrs followed by calcination at 250° C. for 6 hrs under nitrogen flow. The chemical composition of the adsorbent, Sample-11 thus obtained was 30% $Ag_2SO_4$ and 70% $SiO_2$, The adsorbed ethylene was 1.13 mmol of ethylene at 30° C. and 1 atmosphere pressure. The absorbent was able to reabsorb the same amount of ethylene under similar conditions.

EXAMPLE-13

Figure 1B:
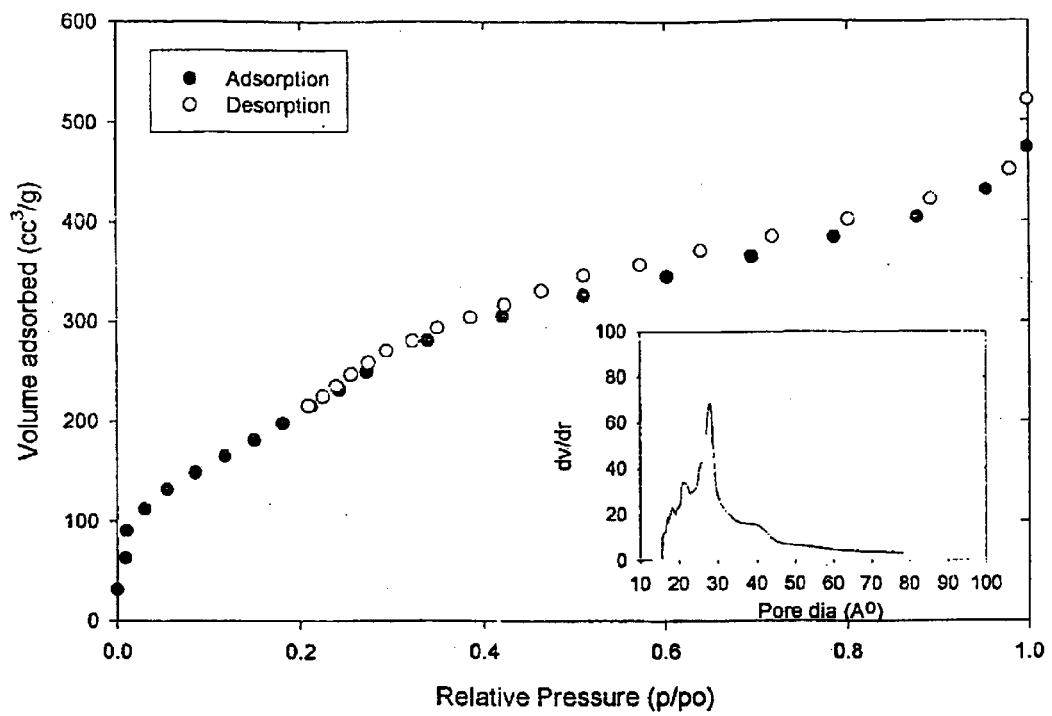
FIG. 1B is a graph showing nitrogen adsorption-desorption data and pore size distribution on HMS (Hexadecylamine) at 77K of an adsorbent of the invention.

A homogeneous solution was obtained by dissolving 6.04 g of hexadecylamine in 82.8 g of ethyl alcohol in a beaker. To this solution 61.2 g of double distilled water was added with vigorous stirring. To the resultant solution, 20.8 g of tetraethyl orthosilicate (TEOS) was slowly added dropwise with continuous stirring at room temperature. Stirring was continued for another 3 hours followed by aging for 24 hours at room temperature. The resultant solid product, hexagonal mesoporous silica, HMS-2 was recovered by filtration and washing with water and water-alcohol mixture. HMS-2 was then air dried followed by oven drying for 10 hours. The resultant mesoporous silica was calcined at 600° C. for 4 hours. The yield of Silica-2 product was 95% by weight. The XRD of the sample exhibited a characteristic peak at 2.4 (2 θ). Surface area (870 $m^2/g$), average pore size (2.8 nm) and pore volume (0.73 cc/g) were obtained from measured $N_2$ adsorption and desorption isotherms at –196° C. (FIG. 1).

EXAMPLE-14

About 0.6 g of silver nitrate was impregnated on activated HMS-2 substrate obtained from Example-13 using the impregnation procedure employed in Example-2. The resultant adsorbent, Sample-12, was dried at 110° C. in an oven for 10 hours followed by activation in a muffle furnace at 200° C. for 4 hours. The chemical composition of the adsorbent is 37.5 wt % $AgNO_3$ and 62.5 wt % $SiO_2$. The adsorbent adsorbed 1.51 and 1.92 mmol/g of ethylene and propylene respectively at 30° C. and 1 atmosphere. Over 93% of olefin adsorption capacity was completed within 5 minutes. On desorption at 30° C. by evacuation only (1 mmHg) 0.14 mmol/g of ethylene was retained on the adsorbent. However, on heating at 100° C. both ethylene and propylene were completely desorbed.

EXAMPLE-15

Figure 1C:
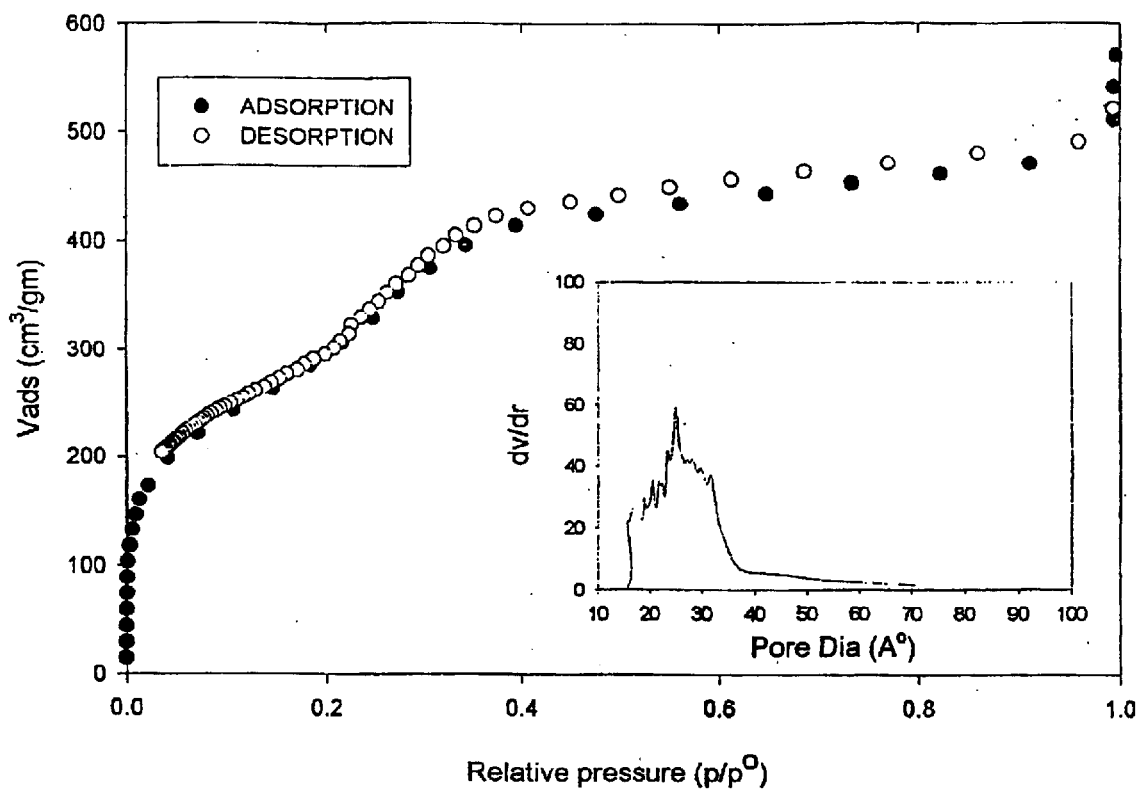
FIG. 1C is a graph showing nitrogen adsorption-desorption isotherms and pore size distribution on HMS (Brij-97) at 77K of an adsorbent of the invention.

A homogeneous solution was obtained by dissolving 4.0 g of Brij-97 (Aldrich) in 20.0 g of water in beaker and 80 g of 2.0 molar hydrochloric acid. To this solution, 8.80 g of tetraethyl orthosilicate (TEOS) was slowly added drop wise with continuous stirring at room temperature. Stirring was continued after the addition of TEOS for another 24 hrs at room temperature. The resultant solid product, hexagonal mesoporous silica HMS-3 was recovered by filtration, washed and air dried at room temperature. HMS-3 was then oven dried for 8 hours followed by calcination at 500° C. for 8 hours. XRD of the above sample showed a characteristic peak at 1.96 (2θ). Surface area (1194 $m_2/g$), average pore size (2.7 nm) and pore volume (1.02 cc/g) were obtained from measured nitrogen adsorption and desorption isotherms at –196° C. (FIG. 1c).

EXAMPLE-16

About 0.4 g of silver nitrate was impregnated on activated substrate, HMS-3obtained from Example-15 using the impregnation procedure employed in Example-2. The resultant adsorbent, Sample-13, was dried at 110° C. in an oven for 10 hours followed by activation in a muffle furnace at 200° C. for 4 hours. The chemical composition of the adsorbent was 30.0 wt % $AgNO_3$ and 70.0 wt % $SiO_2$. The adsorbent adsorbed 1.91 mmol/g of ethylene and 0.38 mmol/g of ethane at 30° C. Adsorption uptake of ethylene was also rapid. Over 90% of adsorption capacity was complete within 5 minutes. On desorption at 30° C. by evacuation only (1 mmHg) 0.14 mmol/g of ethylene was retained on the adsorbent. However, on heating at 100° C. ethylene was completely desorbed.

EXAMPLE-17

About 0.6 g of silver nitrate was impregnated on activated substrate HMS-3 obtained from Example-15 using the impregnation procedure employed in Example-2. The resultant adsorbent, Sample-14, was dried at 110° C. in an oven for 10 hours followed by activation in a muffle furnace at 200° C. for 4 hours. The chemical composition of the adsorbent was 37.0 wt % $AgNO_3$ and 63.0 wt % $SiO_2$. The adsorbent adsorbed 2.16 mmol/g of ethylene and 0.41 mmol/g of ethane at 30° C. Adsorption uptake of ethylene was also rapid. About 90% of adsorption capacity was completed within 5 minutes. On desorption at 30° C. by evacuation only (1 mmHg) 0.18 mmol/g of ethylene was retained on the adsorbent. However, on heating at 100° C. ethylene was completely desorbed.

EXAMPLE-18

About 0.6 g of silver acetate was impregnated on activated HMS-3 obtained from Example-15 using the impregnation procedure employed in Example-2. The resultant adsorbent, Sample-15, was dried at 110° C. in an oven for 10 hours followed by activation in a muffle furnace at 200° C. for 4 hours. The chemical composition of the adsorbent was 37.0 wt % $CH_3COOAg$ and 73.0 wt/0 $SiO_2$. The adsorbent adsorbed 1. mmol/g of ethane at 30° C. Adsorption uptake of ethylene was also rapid. Over 86% of adsorption capacity was complete within 5 minutes. On desorption at 30° C. by evacuation, only (1 mmHg) 0.26 mmol/g of ethylene was retained on the adsorbent.

EXAMPLE-19

Mesoporous silica support was synthesized employing cyclohexyl amine as templating agent. Cyclohexyl amine alcohol solution was prepared by mixing 2.7 g of cyclohexyl amine to 82.8 g of ethyl alcohol. To the resultant solution 61.2 g. of water was-added and mixed thoroughly to obtain a homogeneous solution. To the above solution 20.8 g of tetraethyl orthosilicate was added drop-wise with continuous stirring. The stirring was continued for another 1 hour. To the resultant solution 5 g of 2 molar HCl was added. The stirring was continued for further 1 hour. The gel was aged for 12 hours and the resultant solid silica thus obtained was dried at 110° C. followed by calcination at 600° C. for four hours. The mesoporous silica substrate thus obtained possessed 540 m$^2$/g surface area and 1.04 cc/g pore volume.

Silver nitrate was impregnated on the silica support obtained above using the impregnation procedure employed in Example-2. The resultant adsorbent, Sample-16 was dried at 110° C. in an oven for 10 hours followed by activation in a muffle furnace at 200° C. for 4 hours. The chemical composition of the adsorbent was 30.0 wt % AgNO$_3$ and 70.0 wt % SiO$_2$. The adsorbent adsorbed 1.54 mmol/g of ethylene and 0.48 mmol/g of ethane at 30° C. Adsorbed ethylene was completely desorbed by heating at 100° C.

EXAMPLE-20

Mesoporous silica substrate was synthesized employing Tween-60 (Aldrich, USA). Surfactant solution was prepared by dissolving 1.028 g of Tween-60 in 50 ml water with continuous stirring. To this solution 1.664 g of TEOS was added and stirring continued for 6 hours. The resultant mixture was left overnight for phase separation. The white foam covering the solution was removed and 0.84 ml of 0.238 molar NaF was added to the clear solution with stirring. The gel had a composition TW:0.02 TEOS:0.1'6 NaF:0.004 H$_2$O:55.6 The resultant gel was aged under slow stirring for 48 hours. The white colloidal suspension formed was filtered and dried in air followed by calcination in air at 200° C. for 6 hours and at 620° C. for 6 hours. The hexagonal mesoporous silica support thus obtained possessed 604 m$^2$/g surface area, 0.66 cc/g pore volume.

Silver nitrate was impregnated on the silica support obtained above using the impregnation procedure employed in Example-2. The resultant absorbent, Sample-17, was dried at 110° C. in an oven for 10 hours followed by activation in a muffle furnace at 200° C. for 4 hours. The chemical composition of the adsorbent was 30.0 wt % AgNO$_3$ and 70.0 wt % SiO$_2$. The adsorbent adsorbed 1.48 mmol/g of ethylene and 0.39 mmol/g of ethane at 30° C. Adsorbed ethylene was completely desorbed by heating at 100° C.

EXAMPLE-21

Mesoporous silica substrate was synthesized employing triblock poly(ethylene oxide)-(polypropylene oxide)-(polyethylene oxide) copolymer (EO$_{20}$ PO$_{70}$ EO$_{20}$, Molecular weight 5800) which was dissolved in 32 g of distilled water under stirring. To the resultant solution 118 g of 2M HCl was added under stirring to form a homogeneous solution and finally 8.5 g of tetraethylorthosilicate (TEOS) was added to form gel. The gel was aged at 85° C. without stirring. The solid product was filtered and washed with water at room temperature. The material obtained was dried at 90° C. overnight and calcined at 500° C. for 6 h under air flow.

Silver nitrate was impregnated on SB A-15 support obtained above using the impregnation procedure employed in Example-2. The resultant adsorbent, Sample 18, was dried at 110° C. in an oven for 10 hours followed by activation in a muffle furnace at 220° C. for 4 hours. The chemical composition of the adsorbent is 29.5 wt % AgNO$_3$ and 70.5 wt % SiO$_2$. The adsorbent adsorbed 1.44 and 1.56 mmol/g of ethylene and propylene respectively at 1 atm and 30° C. On the other hand the adsorbent adsorbed only 0.31 and 0.51 mmol/g of ethane and propane respectively. Adsorbed ethylene was completely desorbed by heating at 100° C.

EXAMPLE-22

Mesoporous alumina support is synthesized by the following procedure. Dodecylamine (3.37 g) was dissolved in mixture containing 47.5 g of ethyl alcohol and 35.6 g of double distilled water. The mixture was mixed well for five minutes. To this solution 13.7 g of aluminium isopropoxide was added. The resultant gel was stirred for 30 minutes and aged for 24 hours at room temperature. The mesoporous alumina thus obtained was filtered, washed and dried at room temperature. The alumina was then dried at 110° C. for 10 hours followed by calcination at 500° C. for 4 hours. The mesoporous alumina obtained possessed 300 m$^2$/g surface area and 0.88 cc/g pore volume.

Silver nitrate was impregnated on mesoporous alumina support obtained above using the impregnation procedure employed in Example-2. The resultant adsorbent, Sample-19 was dried at 110° C. in an oven for 8 hours followed by activation in a muffle furnace for 4 hours. The chemical composition of the adsorbent is 30.0 wt % AgNO$_3$ and 70.0 SiO$_2$. The adsorbent adsorbed 0.94 and 0.46 mmol/g of ethylene and ethane respectively at 1 atm and 30° C.

EXAMPLE-23

Mesoporous alumina with lethisin as template was synthesized using 206.6 g of aluminum triisopropoxide (merck). 302 g of ethanol and 80.4 g of isopropanol was added under stirring for 45 minutes in a beaker. 50.0 g of soybean lecithin comprising 40–45% phosphatidyl choline, 10% phosphatidyl ethanloamine and 2% phosphatidyl inositol was added to this mixture in the beaker under stirring. To the mixture, 640 g of distilled water and 7.8 g of 10% HCl solution were added to form a suspension. The resultant suspension was stirred at room temperature for 24 hrs, filtered and air dried in air for 20 hrs. The solid thus recovered was dried in oven at 65° C. for 14 hrs and finally calcined in air at 500° C. for 5 hrs. The resultant alumina exhibited a characteristic XRD peak at 0.756 (26). The mesoporous alumina substrate thus obtained possessed 450 m$^2$/g surface area and 0.89 cc/g pore volume.

Silver nitrate was impregnated on mesoporous alumina support obtained above using the impregnation procedure employed in Example-2. The resultant adsorbent, Sample-20 was dried at 110° C. in an oven for 8 hours followed by activation in a muffle furnace at 200° C. for 4 hours. The chemical composition of the adsorbent is 30.0 wt % AgNO$_3$ and 70.0 wt % SiO$_2$. The adsorbent adsorbed 1.60 mmol/g of ethylene and 0.52 mmol/g of ethane respectively at 1 atm and 30° C.

EXAMPLE-24

About 10 g of the adsorbent Sample-1 prepared in the same manner as described in Example-2 was packed in a stainless steel column of 30 mm height and 7 mm diameter (11.2 ml internal volume). The adsorbent was activated at 200° C. for 2 hrs under helium flow and the temperature was reduced to 28° C. Feed mixture consisting of 70.5% of ethylene and 29.5% of ethane by volume was allowed to pass through the adsorbent bed at 1000 mmHg at a feed flow rate of 50 sccm. In the first 600 sec, the concentration of ethylene in the off gas was lower than 0.1% by volume. The dynamic adsorption capacity of ethylene on the above adsorbent as obtained from the breakthrough curve was 1.57 mmol/g. The adsorbed ethylene could be completely desorbed by evacuation to 30 mmHg at 90C.

EXAMPLE-25

About 10 g of the adsorbent prepared in the manner described in Example-4 was packed in to a stainless steel column of 300 mm height and 7 mm diameter. The adsorbent was activated at 200° C. for 3 hrs under helium flow and the temperature was reduced to 30° C. Feed mixture consisting of 70.4% of ethylene, 29.5% of ethane by volume and traces of carbon dioxide, methane and hydrogen was allowed to pass through the adsorbent bed at 1000 mmHg at a feed flow rate of 50 sccm. When the concentration of ethylene in the off gas increased to 0.1% the feed flow was stopped. The bed was then purged with pure ethylene gas (cocurrent to feed flow) till ethane concentration was reduced to less than 0.05% by volume. The adsorbed ethylene could be completely desorbed (counter current to feed flow) by evacuation to 50 mmHg and 90° C. The feed was again allowed to pass through the bed followed by desorption. After five such adsorption-purge-desorption cycles ethylene concentration in the off gas after 300 sec was lower than 0.01% by volume. The adsorbed ethylene could be completely desorbed by evacuation to 50 mmHg and 90° C. with high purity of >99.5%.

What is claimed is:

1. A process for separating ethylene, propylene or a mixture thereof from a mixed gas comprising the steps of:
   (a) providing an adsorbent comprising a silver or copper compound impregnated on a substrate consisting of mesopores selected from the group consisting of mesoporous silica and mesoporous alumina, the silver or copper compound being present in the adsorbent in an amount of 1 to 70 wt % and the substrate being in the adsorbent in an amount of 30 to 99 wt %;
   (b) passing a mixed gas containing olefin molecules, including the ethylene propylene or mixture thereof, and a component selected from the group consisting of H, $N_2$, Ar, He, $CH_4$, $C_2H_6$, $C_3H_8$, CO, $CO_2$ and a mixture thereof;
   purging the adsorbent bed with an olefin; and
   (c) recovering adsorbed ethylene and/propylene.

2. A process as claimed in claim 1, wherein the recovering in step (c) comprises lowering a pressure on and/or heating the adsorbent.

3. A process as claimed in claim 1, wherein the adsorbent comprises a silver (I) compound selected from the group consisting of silver nitrate, silver perchlorate, silver tetrafluoroborate, silver carboxylate, silver halide, silver sulfate, silver oxide and a mixture thereof.

4. A process as claimed in claim 1, wherein the adsorbent comprises a copper compound selected from the group consisting of copper (I) chloride, copper sulfate and copper acetate.

5. A process as claimed in claim 1, wherein the adsorbent comprises mesoporous alumina having an average pore diameter of 5 to 12 nm and a minimum surface area of 200 $m^2/g$.

6. A process as claimed in claim 1, wherein the substrate is in powder form.

7. A process as claimed in claim 1, wherein the substrate is in a form of formed bodies.

8. A process as claimed in claim 7, wherein the formed bodies have a size in a range of 0.01 to 5 nm.

9. A process as claimed in claim 7, wherein the substrate has been pelletized with inorganic clay.

10. A process as claimed in claim 9, wherein the inorganic clay is selected from the group consisting of alumina, bentonite, attapulgite, sapiolite, kaolinite, sodium silicate and potassium silicate.

11. A process as claimed in claim 1, wherein the adsorbent consists essentially of the silver or copper compound and the substrate.

12. A process as claimed in claim 1, wherein the adsorbent consists of the silver or copper compound and the substrate.

13. A process for separating ethylene, porpylene or a mixture thereof from a mixed gas comprising the steps of:
   (a) providing an adsorbent comprising a silver or copper compound impregnated on a substrate comprising mesoporous silica or mesoporous alumina, the silver or copper compound being present in the adsorbent in an amount of 1 to 70 wt % and the substrate being in the adsorbent in an amount of 30 to 99 wt %;
   (b) passing a mixed gas containing olefin molecules, including the ethylene propylene or mixture thereof, and a component selected from the group consisting of H, N, Ar, He, $CH_4$, $C_2H_6$, $C_3H_8$, CO, $CO_2$ and a mixture thereof;
   purging the adsorbent bed with an olefin; and
   (c) recovering adsorbed ethylene and/propylene wherein the adsorbent comprises mesoporous silica selected from the group consisting of hexagonal mesoporous silica and SBA-15, the mesoporous having an average pore diameter of 2 nm to 10 nm and minimum surface area of 200 $m^2/g$.

14. An adsorbent for selective adsorption of unsaturated hydrocarbons comprising a silver or copper compound in an amount of 1 to 70 wt % and a substrate consisting of mesopores selected from the group consisting of mesoporous silica and mesoporous alumina in an amount of 30 to 99 wt %.

15. An adsorbent as claimed in claim 14, wherein the silver compound is a silver (I) compound selected from the group consisting of silver nitrate, silver perchlorate, silver tetrafluoroborate, silver carboxylate, silver halide, silver sulfate, silver oxide and a mixture thereof.

16. An adsorbent as claimed in claim 14, wherein the copper compound is selected from the group consisting of copper (I) chloride, copper sulfate and copper acetate.

17. An adsorbent as claimed in claim 14, wherein the substrate is mesoporous alumina having an average pore diameter of 5 to 12 nm and a minimum surface area of 200 $m^2/g$.

18. An adsorbent as claimed in claim 14, wherein the mesoporous substrate is in powder form.

19. An adsorbent as claimed in claim 14, wherein the mesoporous substrate is in a form of formed bodies.

20. An adsorbent as claimed in claim 19, wherein the formed bodies have sizes within a range of 0.01 to 5 nm.

21. An adsorbent as claimed in claim 19, wherein the substrate has been pelletized with inorganic clay.

22. An adsorbent as claimed in claim 21, wherein the inorganic clay is selected from the group consisting of alumina, bentonite, attapulgite, sapiolite, kaolinite, sodium silicate and potassium silicate.

23. An adsorbent as claimed in claim 14, wherein the adsorbent consists essentially of the silver or copper compound and the substrate.

24. An adsorbent as claimed in claim 14, wherein the adsorbent consists of the silver or copper compound and the substrate.

25. An adsorbent for selective adsorption of unsaturated hydrocarbons comprising a silver or copper compound in an amount of 1 to 70 wt % and a substrate selected from the group consisting of mesoporous silica and mesoporous alumina in an amount of 30 to 99 wt %, wherein the substrate is mesoporous silica selected from the group consisting of hexagonal mesoporous silica and SBA-15, said mesoporous silica having an average pore diameter of 2 nm to 10 nm and a minimum surface area of 200 m$^2$/g.

26. A method for the manufacture of an adsorbent comprising impregnating or dispersing a silver (I) compound or a copper (I) compound on a substrate consisting of mesopores selected from the group consisting of mesoporous silica and mesoporous alumina to form a composite material and drying the composite material by heat treatment.

27. A method as claimed in claim 26, wherein the substrate is impregnated or dispersed with a silver (I) compound selected from the group consisting of silver nitrate, silver perchlorate, silver tetrafluoroborate, silver carboxylate, silver halide, silver sulfate, silver oxide and a mixture thereof.

28. A method as claimed in claim 26, wherein the substrate is impregnated or dispersed with a copper (I) compound selected from the group consisting of copper (I) chloride, copper sulfate and copper acetate.

29. A method as claimed in claim 26, wherein the silver (I) compound is in the form of a solution comprising a solvent selected from the group consisting of water, aqueous hydrochloric acid solution, aqueous nitric acid solution, ammonium hydroxide solution, primary or secondary alcohols having 1 to 7 carbon atoms, acetone, ethyl acetate, C4 to C7 hydrocarbons, propionitrile and acetonitrile.

30. A method as claimed in claim 26, wherein the silver (I) compound or the copper (I) compound is impregnated on the substrate by physically mixing the silver (I) compound or the copper (I) compound in a sold form with the support in powder form.

31. A method as claimed in claim 26, wherein the adsorbent comprises the silver (I) compound or the copper (I) compound in an amount from 1 to 70 wt %.

32. A method as claimed in claim 26, wherein the composite material is dried at a temperature in the range of 90 to 110° C.

33. A method as claimed in claim 26, wherein the dried composite material is calcined at a temperature in the range of 30 to 600° C.

34. A method as claimed in claim 33, wherein the dried composite material is calcined at a temperature in the range of 100–250° C.

35. A method as claimed in claim 34, wherein the calcination is carried out for a period in the range of 0.1 to 100 hours.

36. A method as claimed in claim 35, wherein the calcination is carried out for a period in the range of 1 to 10 hours.

37. A method as claimed in claim 26, wherein the mesoporous substrate is mesoporous alumina having an average pore diameter of 5 to 12 nm and a minimum surface area of 200 m$^2$/g.

38. A method as claimed in claim 26, wherein the mesoporous substrate is in powder form.

39. A method as claimed in claim 26, wherein the mesoporous substrate is in a form of formed bodies.

40. A method as claimed in claim 39, wherein the formed bodies have a size in a range of 0.01 to 5 nm.

41. A method as claimed in claim 39, wherein the substrate has been pelletized with inorganic clay.

42. A method as claimed in claim 41, wherein the inorganic clay is selected from the group consisting of alumina, bentonite, attapulgite, sapiolite, kaolinite, sodium silicate and potassium silicate.

43. A method for the manufacture of an absorbent comprising impregnating or dispersing a silver (I) compound or a copper (I) compound on a mesoporous substrate selected from the group consisting of mesoporous silica and mesoporous alumina to form a composite material and drying the composite material by heat treatment, where the mesoporous silica is selected from the group consisting of hexagonal mesoporous silica and SBA-15, the mesoporous silica having an average pore diameter of 2 nm to 10 nm and a minimum surface area of 200 m$^2$/g.

* * * * *